United States Patent [19]
Vander Zwan et al.

[11] 4,092,314
[45] May 30, 1978

[54] PREPARATION OF 4,6-DIAMINO-5-ARYLAZOPYRIMIDINES AND ADENINE COMPOUNDS

[75] Inventors: Michael C. Vander Zwan, Somerset; Donald F. Reinhold, North Plainfield, both of N.J.

[73] Assignee: Merck & Co., Inc., Rahway, N.J.

[21] Appl. No.: 733,489

[22] Filed: Oct. 18, 1976

Related U.S. Application Data

[63] Continuation-in-part of Ser. No. 593,910, Jul. 7, 1975, abandoned.

[51] Int. Cl.² .............................................. C07D 473/34
[52] U.S. Cl. ...................................... 544/277; 260/154
[58] Field of Search ................................ 260/154, 252

[56] References Cited

FOREIGN PATENT DOCUMENTS 81,394/74  8/1974  Japan.
28,497/73  4/1973  Japan.

Primary Examiner—Paul M. Coughlan, Jr.
Attorney, Agent, or Firm—Walter Patton

[57] ABSTRACT

The present invention relates to a novel and useful process for preparing 4,6-diamino-5-arylazopyrimidine from an arylazomalononitrile in the presence of ammonium chloride and formamide. If desired, the 4,6-diamino-5-arylazopyrimidine may then be hydrogenated to form 4,5,6-triaminopyrimidine which, when the hydrogenation is carried out in the presence of formic acid or its derivative, gives adenine.

10 Claims, No Drawings

PREPARATION OF 4,6-DIAMINO-5-ARYLAZOPYRIMIDINES AND ADENINE COMPOUNDS

This application is a continuation-in-part application of co-pending application U.S. Ser. No. 593,910 filed Jul. 7, 1975, now abandoned.

BACKGROUND OF THE INVENTION

Adenine or 6-aminopurine, is a naturally occurring product which is well known as an intermediate in the formation of various final products (see U.S. Pat. No. 3,846,246). It is known in the art that adenine may be prepared from 4,6-diamine-5-arylazopyrimidine [see Baddiley et al., "Jour. of the Chem. Soc." Part II (1943) pg. 386–387 and Cavalieri et al., "Jour. of the Am. Chem. Soc." Vol. LXXI (January–April 1949) pg. 533–536]. It is taught in Japanese patent publication No. 28497/73 application No. 62028/71 filed Aug. 17, 1971 and published April 14, 1973 that adenine may be prepared by a catalytic reduction of arylazomalononitrile in formamide in the presence of ammonia to obtain adenine in a single process step. It has been found, however, that the product resulting from said process leaves much to be desired in purity and yields. It has now been found that when a similar process is carried out in two stages, the yield and purity of the final product is substantially improved.

SUMMARY OF THE INVENTION

It is an object of the present invention to produce 4,6-diamino-5-arylazopyrimidine in good yields and high purity. A further object is to hydrogenate the intermediate 4,6-diamino-5-arylazopyrimidine in the presence of formic acid or its derivative such as the ester or amide to form adenine in good yields and high purity.

A still further object is to prepare adenine directly from arylazomalononitrile without the isolation of the intermediate 4,6-diamino-5-arylazopyrimidine. Another object is to provide a relatively simple process for the formation of adenine. Other objects will become apparent as the description of the invention proceeds.

DESCRIPTION OF THE PREFERRED EMBODIMENTS

These objects are accomplished by the present invention which provides a process for preparing 4,6-diamino-5-arylazopyrimidine which comprises reacting arylazomalononitrile with formamide and ammonia in the presence of ammonium salt as a catalyst.

The reaction of the present invention is carried out in a solvent such as methanol, ethanol, isopropanol, cyclic and acyclic ethers, methylene chloride, ethylene dichloride, hexane, octane, decane and the like. The nature of the solvent is not at all critical but in a preferred embodiment of the present invention, formamide is used as the solvent and a considerable excess is employed, i.e., 10–20 moles per mole of arylazomalononitrile. Since only 1 mole is needed for the reaction, the excess is utilized merely as a solvent. The ammonium salts used in the practice of this invention include the ammonium salts of any inorganic or organic acid. For example, it includes ammonium acetate, sulfate, iodide, chloride, ammonium carbonate, ammonium propionate, ammonium benzoate, ammonium nitrate and the like. Preferably, the salt is an ammonium halide since the salts are inexpensive and readily available. The ammonium salts are generally used in amounts of at least 0.1% by weight based on the weight of the arylazomalononitrile and more preferably from 5 to 100%. In a more preferred embodiment the amount is 10 to 60%.

The temperature to be employed for the reaction is generally from about 50° to about 400° C., but this may be varied as desired. For example, if an unusually long reaction time is not a disadvantage, room temperature may be employed but it may require many days for the reaction to go to completion. Under ordinary circumstances a temperature of about 90° to about 250° C. is employed and a preferred range is 140° to 160° C.

In carrying out the reaction, at least 1 mole of ammonia is used per mole of arylazomalononitrile if optimum yields are desired. While lesser amounts can be used, the reaction requires 1 mole and any lesser amount will result in reduced yields. Based on the weight of the arylazomalononitrile, the ammonia should be present in amounts of from about 10 to about 300%, more preferably 25 to 100% by weight. Generally, 50 to 90% will be employed.

The term "aryl" as used herein signifies any organic radical derived from an aromatic hydrocarbon. It also includes such radicals containing substituent groups such as amino, halo, alkyl, nitro, hydroxy, alkoxy, aryloxy, carboxyl, cyano and the like. In the preparation of adenine, the aryl group is removed in the final reaction and the nature of this substituent is not at all critical. Substituent groups may even be employed which enter into the reaction since those only result in impurities being formed when the aryl group is removed. Preferably, the aryl group is unsubstituted.

The present invention also provides a process for preparing adenine which comprises reacting arylazomalononitrile with formamide and ammonia in the presence of an ammonium salt to form 4,6-diamino-5-arylazopyrimidine and thereafter hydrogenating the 4,6-diamino-5-arylazopyrimidine in the presence of formic acid or its derivatives, such as the ester or amide, to form adenine.

The term "thereafter" signifies that the reaction of the arylazomalononitrile to form the 4,6-diamino-5-arylazopyrimidine is allowed to go to substantial completion before the pyrimidine compound is hydrogenated to form adenine. In other words, the hydrogenation reaction is not carried out at the same time as the formation of pyrimidine which gives better yields and purity.

In carrying out the hydrogenation reaction, any solvent may be used as given above but again it is preferred that formamide be used as the solvent. Since 2 moles of formamide are required in the reaction for each mole of pyrimidine compound, it is preferred to use from about 4 to about 20 moles of formamide as reactant and solvent. With the solvent the same for both reactions, this means that the intermediate product need not be isolated. Preferably a hydrogenation catalyst is employed in the reaction in amounts of from about 0.1 to 10% based on the weight of the pyrimidine compound. In a preferred embodiment of the present invention, the catalyst is used in amounts from 0.5 to 2.5% and generally about 1% is employed. The hydrogenation catalyst can be any of the well known catalysts and includes platinum, nickel, Raney nickel, and copper, rhodium, rutherium, and all other metals contained in Groups VIII, IB, IIB, VB, VIB and VIIB of the Periodic Table. Other hydrogenation catalysts may be selected as desired.

The following examples are given to illustrate the invention and are not intended to limit it in any manner. All parts are expressed in part by weight unless otherwise indicated.

EXAMPLE 1

Preparation of 4,6-Diamino-5-phenylazopyrimidine

A 300 ml. autoclave was sequentially charged with 2.12 g. of ammonium chloride (0.04 mole), 17.0 g. of phenylazomalononitrile (0.10 mole), and 92 ml. of formamide. The system was flushed with ammonia, sealed, and then saturated with ammonia to 10 psi. The system was then heated (and stirred at 1000 rpm) to 150° C. for 5 hours with occasional venting to maintain 40–50 psi. After cooling to room temperature, excess ammonia was sparged with nitrogen, the orange solids were filtered (mother liquors were used for all transfers and saved for re-cycling), and the cake was displaced first with 12 ml. of fresh formamide then with 10 ml. of water. The cake was vacuum oven dried (100° C., 20 mm Hg, 3 hours) and gave 19.55 g. of 4,6-diaminophenylazopyrimidine (91.4% yield); U.V. (0.1M HCl in methanol) $\lambda$max 370, E% = 893, m.p. 295°–300° C., eq. wt. (HClO$_4$) 216.3 (99.0% pure), tlc (silica gel, CHCl$_3$:MeOH::6:1 by vol.): single spot.

EXAMPLE 2

Preparation of Adenine from Phenylazomalononitrile

A glass liner is charged with 20 ml. of ethyl alcohol, 4.5 g. of formamide, 0.53 of ammonium chloride, 4.25 g. of phenylazomalononitrile, 4 g. of ammonia and 0.15 g. of Raney nickel. The system is sealed and heated to 150° C. and aged at that temperature with rocking for 4 hours. After this point a charge of 1300–1400 psi of H$_2$ is applied to the system and the reaction is continued (at 150° C. with rocking) for an additional 8 hours. After cooling to room temperature, the volatile material is distilled off and the residue is dissolved in water containing 0.40 g. of sodium hydroxide. After swirling for 20 minutes, the insoluble catalyst is filtered off. The filtrate is worked up in the usual fashion (i.e., acidifying to pH 7.0 with HCl and filtering off solids) to give material which after vacuum oven drying at 80° C. amounts to 3.0 g. This material has an identical R$_f$ as adenine on tlc and is single spot material. The U.V. (N/10 HCl)$\lambda$max 263, E% 822 indicates 85% purity. Liquid chromatography (L.C.) compared to analytical adenine indicates 73.8% purity. L.C. also indicates that the filtrate contains an additional 0.25 g. of adenine. Total yield corrected for purity (3.0) (0.738) + 0.25 g. equals 2.47 g. or 73%.

EXAMPLE 3

Preparaton of 4,6-Diamino-5-phenylazopyrimidine

Example 1 is repeated exactly as described except no ammonium chloride is added. After an identical work-up there is obtained 19.5 g. (yield 91.16%) of lower quality 4,6-diamino-5-phenylazopyrimidine, U.V. (0.1N HCl)$\lambda$max = 368, E% = 786; m.p. 280°–297° C.; eq. wt. (HClO$_4$) 224.8 (95.3% pure) tlc, silica gel (CHCl$_3$:MeOH::6:1, by vol.): trace two impurities. This example shows that without the ammonium salt a lower yield is obtained and the product is impure.

EXAMPLE 4

Preparation of 4,6-Diamino-5-phenylazopyrimidine

Example 1 is repeated exactly as described except ammonium acetate is added. After an identical work-up there is obtained 19.92 g. of 4,6-diamino-5-phenylazopyrimidine (93.2%): U.V. (0.1N HCl)$\lambda$max = 365, E% = 773; m.p. 298°–300° C.; eq. wt. (HClO$_4$) 218; tlc, silica gel (CHCl$_3$:MeOH::6:1, by vol.): single spot. The example shows that other ammonium salts are suitable for the reaction.

EXAMPLE 5

Preparation of 4,6-Diamino-5-phenylazopyrimidine

Example 1 is repeated exactly as described except ammonium iodide is added. After an identical work-up there is obtained 19.20 g. of 4,6-diamino-5-phenylazopyrimidine (89.7%): U.V. (0.1N HCl)$\lambda$max = 365, E% = 817; m.p. 299°–302° C.; eq. wt. (HClO$_4$) 213.8; tlc, silica gel (CHCl$_3$:MeOH::6:1, by vol.): single spot. The Example shows that other ammonium salts are suitable for the reaction.

EXAMPLE 6

Preparation of 4,6-Diamino-5-phenylazopyrimidine

Example 1 is repeated exactly as described except ammonium sulfate is added. After an identical work-up there is obtained 19.6 g. of 4,6-diamino-5-phenylazopyrimidine (91.4%): U.V. (0.1N HCl)$\lambda$max = 365, E% = 808; m.p. 293°–297° C.; eq. wt. (HClO$_4$) 217.6; tlc, silica gel (CHCl$_3$:MeOH::6:1, by vol.): single spot. The Example shows that other ammonium salts are suitable for the reaction.

EXAMPLE 7–10

Example 1 is repeated with the exception that the reaction is carried out at various temperatures as shown in the following table.

| Example | Temp. (° C.) | Wt. Yield (grams) | % Yield | m.p. (° C.) | Eq. Wt. (HClO$_4$) | U.V. (0.1N HCl) ($\lambda_{max}$ 365) |
|---|---|---|---|---|---|---|
| 7 | 90 | 17.0 | 79.4 | 255–264 | 190.4 | 1090 |
| 8 | 120 | 18.5 | 86.5 | 252–259 | 206.7 | 863 |
| 9 | 250 | 13.2 | 61.8 | 299–305 | 214.8 | 785 |
| 10 | 25 | Some material by tlc. | | | | |

The table shows that the reaction may be carried out over a wide range of temperature conditions. Preferably the temperature is in the range of 90° to 250° C.

EXAMPLE 11

Preparation of Adenine from 4,6-Diamino-5-arylazopyrimidine

A 300 ml. autoclave is charged sequentially with 24 ml. of formamide (27 g., 0.6 mole), 21.42 g. of 4,6-diamino-5-phenylazopyrimidine (0.1 mole), 80 ml. of isopropanol alcohol, and 240 mg. of 5% Pd/C. The system is sealed and pressurized with 1200 psi of hydrogen, heated to 200° C. and rocked for 8 hours. The vessel is then cooled to room temperatue and the pale yellow adenine is filtered (all transfers are done with mother liquors). The cake is dissolved in 50 ml. of 2N sodium hydroxide solution. The reduction catalyst is filtered off and the filtrate is neutralized to pH 7.0. The white adenine is collected on a funnel and washed with 20 ml. of water. After vacuum over drying (100° C., 20 mm Hg, 3 hours) there is obtained 12.75 g. of adenine (yield 94.5%): U.V. (0.1N HCl)λmax = 263, E% = 928; m.p. >358° C., liquid chromatography, wt. % adenine = 94.7% pure; tlc, silica gel (CHCl$_3$: MeOH::6:1 by vol.): single spot.

EXAMPLE 12

Preparation of Adenine Without Isolation of 4,6-Diamino-5-phenylazopyrimidine

A 300 ml. capacity autoclave is sequentially charged with 2.13 g. of ammonium chloride (0.04 mole), 17.0 g. of phenylazomalononitrile (0.10 mole), 240 mg. of 5% Pd/C and 92 ml. of formamide which contains 12% ammonia by weight. The system is rocked at 150° C. for 5 hours and then charged with H$_2$ to 1200 psi. After aging (with rocking) at this temperature for an additional 5 hours, the system is cooled to room temperature. Identical work-up as described for adenine in Example 11 affords 10.8 g. of adenine (yield 80%) U.V. (0.1N HCl)λmax = 263, E% = 900, m.p. >355° C., L.C. wt. % adenine = 92% pure, tlc single spot.

This Example illustrates that when the reaction of the phenylazomalononitrile to form the 4,6-diamino-5-phenylazopyrimidine is allowed to go to substantial completion before the introduction of H$_2$ pure adenine in high yield is obtained. When the reaction is carried out with H$_2$ present from the start of the reacton the yield of adenine is substantially reduced as illustrated in Example 13.

EXAMPLE 13

Preparation of Adenine from Phenylazomalononitrile

When Example 12 is repeated except that the hydrogen is present from the start of the reaction, there is obtained (by an identical work-up) 13.5 g. of crude material which contains 11.4% adenine by high pressure liquid chromatography assay (or 1.53 g. of adenine) representing a 45% yield. This material is too impure for a melting point and tlc reveals the presence of several contaminants.

Many other equivalent modifications will be apparent to those skilled in the art from a reading of the foregoing without a departure from the inventive concept.

What is claimed is:

1. A process for preparing 4,6-diamino-5-phenylazopyrimidine which comprises reacting phenylazomalononitrile with formamide and at least 1 mole of ammonia per mole of phenylazomalononitrile in the presence of an ammonium salt wherein the ammonium salt is present in an amount of at least 0.1% by weight based on the weight of the phenylazomalononitrile, wherein the reaction is carried out at a temperature of from about 50° to about 400° C. wherein the ammonium salt is selected from the group consisting of ammonium acetate, ammonium sulfate, ammonium iodide, ammonium chloride, ammonium carbonate, ammonium propionate, ammonium benzoate and ammonium nitrate.

2. The process of claim 1 wherein the reaction is carried out at a temperature of from about 90° to about 250° C.

3. The process of claim 1 wherein the reaction is carried out at a temperature of from about 140° to about 160° C.

4. The process of claim 1 wherein the ammonium salt is present in the amount of 5 to 100% by weight based on the weight of the phenylazomalononitrile.

5. The process of claim 1 wherein the ammonium salt is present in the amount of 10 to 60% by weight based on the weight of the phenylazomalononitrile.

6. A process for preparing adenine which comprises reacting phenylazomalononitrile with formamide and ammonia in the presence of an ammonium salt wherein the ammonium salt is present in an amount of at least 0.1% by weight based on the weight of the phenylazomalononitrile to form 4,6-diamino-5-phenylazopyrimidine and thereafter hydrogenating the 4,6-diamino-5-phenylazopyrimidine to form adenine wherein the ammonium salt is selected from the group consisting of ammonium acetate, ammonium sulfate, ammonium iodide, ammonium chloride, ammonium carbonate, ammonium propionate, ammonium benzoate and ammonium nitrate.

7. A process according to claim 6 for preparing adenine which comprises reacting phenylazomalononitrile with formamide and ammonia in the presence of an ammonium salt at a temperature of from about 50° to about 400° C. to form 4,6-diamino-5-phenylazopyrimidine and thereafter catalytically hydrogenating the 4,6-diamino-5-phenylazopyrimidine to form adenine.

8. The process of claim 7 wherein the temperature is from 100° to about 200° C.

9. The process of claim 7 wherein the temperature is from about 140° to about 160° C.

10. The process of claim 9 wherein the 4,6-diamino-5-phenylazopyrimidine is hydrogenated without separation from the reaction mixture in which it is formed.

* * * * *